United States Patent [19]

Slaugh et al.

[11] Patent Number: 5,043,515

[45] Date of Patent: Aug. 27, 1991

[54] ETHYLENE OLIGOMERIZATION CATALYST AND PROCESS

[75] Inventors: Lynn H. Slaugh, Cypress, Tex.; Galeon W. Schoenthal, Cloverdale, Calif.

[73] Assignee: Shell Oil Company, Houston, Tex.

[21] Appl. No.: 389,476

[22] Filed: Aug. 8, 1989

[51] Int. Cl.$^5$ .......................... C07C 2/24; C07C 2/02; B01J 37/00

[52] U.S. Cl. ............................ 585/512; 585/523; 502/117; 526/165; 526/182; 526/184

[58] Field of Search ............... 502/117; 585/512, 523; 526/182, 184, 165

[56] References Cited

U.S. PATENT DOCUMENTS

| | | | |
|---|---|---|---|
| 3,242,099 | 3/1966 | Manyik et al. | 526/165 |
| 3,300,458 | 1/1967 | Manyik et al. | 260/88.2 |
| 4,055,634 | 10/1977 | Brenner et al. | 424/47 |
| 4,404,344 | 9/1983 | Sinn et al. | 526/160 |
| 4,530,914 | 7/1985 | Ewen et al. | 502/113 |
| 4,542,199 | 9/1985 | Kaminsky et al. | 526/160 |
| 4,544,762 | 10/1985 | Kaminsky et al. | 556/179 |
| 4,658,078 | 4/1987 | Slaugh et al. | 585/512 |
| 4,659,685 | 4/1987 | Coleman III et al. | 502/117 |
| 4,665,047 | 5/1987 | Slaugh et al. | 502/108 |
| 4,665,208 | 5/1987 | Welborn, Jr. et al. | 502/117 |
| 4,701,432 | 10/1987 | Welborn, Jr. | 502/117 |
| 4,704,491 | 11/1987 | Tsutsui et al. | 585/523 |
| 4,730,071 | 3/1988 | Schoenthal et al. | 556/179 |
| 4,730,072 | 3/1988 | Schoenthal et al. | 556/179 |
| 4,752,597 | 6/1988 | Turner | 502/104 |
| 4,769,510 | 9/1988 | Kaminsky et al. | 585/523 |
| 4,772,736 | 9/1988 | Edwards et al. | 526/165 |
| 4,791,180 | 12/1988 | Turner | 502/103 |
| 4,808,561 | 2/1989 | Welborn | 502/104 |
| 4,814,540 | 3/1989 | Watanabe et al. | 585/523 |
| 4,841,004 | 6/1989 | Kaminsky et al. | 502/117 |
| 4,849,487 | 7/1989 | Kaminsky et al. | 502/103 |

FOREIGN PATENT DOCUMENTS

| | | | |
|---|---|---|---|
| 87/03604 | 6/1987 | PCT Int'l Appl. | |
| 0793972 | 1/1981 | U.S.S.R. | 585/512 |
| 1044305 | 9/1966 | United Kingdom | 526/165 |

*Primary Examiner*—H. M. S. Sneed
*Assistant Examiner*—J. Saba

[57] ABSTRACT

This invention relates to an oligomerization catalyst comprising a zirconocene and one or more alkyl aluminoxanes wherein the alkyl is selected from methyl, ethyl and mixtures thereof and the ratio of equivalents of methyl to ethyl in the product ranges from about 4 to about 0.25 and wherein the atom ratio of aluminum to zirconium ranges from about 1 to about 100. It further relates to the method for preparing the catalyst and the use of the catalyst in an oligomerization process. The catalyst is particularly suited for the oligomerization of ethylene.

28 Claims, No Drawings

ETHYLENE OLIGOMERIZATION CATALYST AND PROCESS

FIELD OF THE INVENTION

This invention relates to a zirconocene/aluminoxane catalyst for oligomerizing olefins, the process for making the catalyst and the oligomerization process using said catalyst.

BACKGROUND OF THE INVENTION

Metallocene/alumoxane catalysts are known in the art for producing polymers from alpha olefins. Kaminsky, in *Chemical and Engineer News*, July 4, 1983, pp 29–30 and in *Makromol. Chem., Rapid Commun.* 4, 417–421 (1983) discloses zirconium and titanium metallocenes in combination with alumoxanes as catalysts for the polymerization of olefins. Sinn et al in U.S. Pat. No. 4,404,344, issued Sept. 13, 1983 discloses the use of zirconium metallocenes in combination with alumoxanes as olefin polymerization catalysts. Kaminsky et al in U.S. Pat. No. 4,542,199, issued Sept. 17, 1985 discloses the use of a zirconium metallocene in combination with alumoxanes as olefin polymerization catalysts. Turner et al in PCT Application No. US86/02667, published June 18, 1987, discloses the use of Group IVB, VB, VIB and VIII metallocenes in combination with alumoxane as olefin polymerization catalysts. Ewen et al in U.S. Pat. No. 4,530,914, issued July 23, 1985, discloses the use of at least two metallocenes in combination with alumoxane for polymerization of ethylene to products with a broad molecular weight distribution Slaugh et al, in U.S. Pat. No. 4,658,078, issued Apr. 14, 1987, discloses the use of an olefin dimerization catalyst comprising a zirconium or hafnium metallocene combined with an alumoxane wherein the ratio of aluminum to zirconium or hafnium ranges from 1 to 100. Applicants' catalyst oligomerizes lower molecular weight olefins to make oligomers rather than polymers.

SUMMARY OF THE INVENTION

This invention relates to an olefin oligomerization catalyst comprising the reaction product of a zirconocene and one or more alkyl aluminoxanes wherein the alkyl is selected from methyl, ethyl and mixtures thereof and the ratio of equivalents of methyl to ethyl in the product ranges from about 4 to about 0.25 and wherein the atom ratio of aluminum to zirconium ranges from about 0.1 to about 100. It further relates to the process for making the catalyst as well as an oligomerization process. The catalyst is particularly suited to the oligomerization of ethylene to detergent range olefins.

DETAILED DESCRIPTION OF THE INVENTION

The present invention is directed to a catalyst and process for oligomerizing ethylene or ethylene in combination with lower molecular weight alpha olefins into higher molecular weight oligomers. These oligomers are useful as intermediates in preparing, for example, specialty detergents or lubricant additives.

The catalysts of the instant invention are utilized to convert ethylene or ethylene in combination with alpha olefins having carbon numbers ranging from 3 to about 10 to higher oligomers, e.g., dimers, trimers, tetramers, etc. Generally, oligomers of carbon numbers of up to about 30 are desirably produced, more preferably of up to about 25 and even more preferably of up to about 20.

When ethylene is utilized alone, the major proportion of the product olefins are alpha olefins. The instant catalyst and process and process are particularly suitable for converting ethylene to additive range ($C_4$–$C_8$) and detergent range ($C_{10}$–$C_{20}$) olefins.

When as starting material ethylene is used in combination with alpha olefins of $C_3$ or greater, that is when the additional olefin is represented by $RCH=CH_2$ wherein R is alkyl of up to about 8 carbon atoms, the product olefins contain significant portions of vinylidene olefins.

The oligomerization reaction is carried out in a conventional fashion. It may be carried out continuously in a stirred tank reactor wherein olefin and catalyst or catalyst precursors are aided continuously to a stirred tank and reactant, product and catalyst and unused reactant are removed from the stirred tank with the product separated and the catalyst and unused reactant recycled back to the stirred tank. Alternatively, the reaction may be carried out in a batch reactor, wherein the catalyst, or the catalyst precursors, and reactant olefin are charged to an autoclave, and after being reacted for an appropriate time, product is separated from the reaction mixture by conventional means, such as distillation. The reaction is operable over a range of temperatures from about 100° C. to about 130° C., preferably in the range of about 110° C. to about 125° C., more preferably in the range of about 115° C. to about 120° C. Pressures are not critical and can range from about 1 to about 500 atmospheres or higher. The oligomerization reaction can be carried out in the gas phase or liquid phase or mixed gas-liquid phase, depending on the volatility of the feed and product olefins.

The oligomerization may be carried out in the presence of an inert solvent which also may be the carrier for the catalyst and/or feed olefin. Suitable solvents comprise hydrocarbons, such as the alkanes and aromatics, such as benzene, xylene, toluene and the like.

The catalyst of the instant invention has a certain adverse sensitivity to oxygen. It is thus desired to carry the catalyst preparation and oligomerization reaction in the absence of oxygen.

The zirconocenes employed in the production of the catalyst product are organometallic compounds which are cyclopentadienyl derivatives of zirconium and include mono-, di- and tricyclopentadidienyls and their derivatives of zirconium. A preferred zirconocene has the general formula

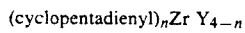

$$(cyclopentadienyl)_n Zr\ Y_{4-n}$$

wherein n is an integer ranging from 1 to 4, Y is selected from the group consisting of hydrogen, a $C_1$–$C_5$ alkyl group, a $C_6$–$C_{20}$ aryl group, or halogen.

Illustrative, but non-limiting examples of the suitable zirconocenes are bis(cyclopentadienyl)zirconium dichloride, bis(cyclopentadienyl)zirconium methyl chloride, bis(cyclopentadienyl)zirconium dimethyl, bis(methylcyclopentadienyl)zirconium dichloride, bis(methylcyclopentadienyl)zirconium methyl chloride, bis(methylcyclopentadienyl)zirconium dimethyl, bis(pentamethylcyclopentadienyl)zirccnium dichloride, bis(pentamethylcyclopentadienyl)zirconium methyl chloride, bis(pentamethylcyclopentadienyl)zirconium dimethyl bis(n-butyl-cyclopentadienyl)zirconium dichloride, bis(n-butylcyclopentadienyl)zirconium methyl chloride, bis(n-butyl-cyclopentadienyl)zirconium dimethyl.

The aluminoxanes (or alumoxanes) are well known in the art and are polymeric alkyl aluminum compounds which can be represented by the general formula $(R-Al-O)_n$, which is a cyclic compound, and $R(R-Al-O)_nAlR_2$, which is a linear compound. In the general formula, R is a methyl and/or ethyl group and n is an integer from 1 to about 40, preferably about 1-2. Generally, in the preparation of aluminoxanes from, for example, trimethyl aluminum and water, a mixture of the linear and cyclic compounds are obtained.

The alkyl aluminoxanes can be prepared in various ways. Preferably, they are prepared by contacting water with a solution of trialkyl aluminum, such as, for example, trimethyl aluminum, in a suitable organic solvent such as benzene or an aliphatic hydrocarbon. The solvents that can be used are well-known and include the saturated aliphatic compounds such as butane, pentane, hexane, heptane, octane, isoctane, the purified kerosenes, etc.; the cycloaliphatics such as cyclobutane, cyclopentane, cyclohexane, cycloheptane, methylcyclopentane, dimethylcyclopentane, etc.; the aromatic solvents such as benzene, toluene, xylene, etc., and the like. The major requirements in the selection of a solvent are that it be liquid at reaction temperatures and pressures, that it does not react with water or the aluminoxanes or interfere with the desired dimerization reaction. The solvent must be oxygen-free. Hydroxy, ether, carboxyl, keto, and the like groups adversely affect aluminoxane production. A particularly suitably solvent is one or more of the olefins to be oligomerized, if the olefin is a liquid. For example, the alkyl aluminum is treated with water in the form of a moist solvent or the alkyl aluminum can be desirably contacted with a hydrated salt such as hydrated copper sulfate or aluminum sulfate.

The aluminoxane can be prepared in the presence of a hydrated copper sulfate. This method comprises treating a dilute solution of trimethyl aluminum in, for example, toluene, with copper sulfate represented by the general formula $CuSO_4.5H_2O$. The ratio of cooper sulfate to trimethyl aluminum is desirably about 1 mole of copper sulfate for 5 moles of trimethyl aluminum. The reaction is evidenced by the evolution of methane. The use of ferrous sulfate heptahydrate as a hydrating agent for trimethylaluminum is disclosed in PCT application US86/02667, incorporated by reference herein.

In general, the mole ratio of alkyl aluminum to water will be 1:1 although variations of this ratio can occur without adversely affecting the aluminoxane product., i.e., the Al/water ratio can vary between about 0.66:1 to about 2:1, preferably between about 0.75:1 to about 1.25:1. A continuous method for producing aluminoxanes is given in U.S. Pat. No. 3,300,458, issued Jan. 24, 1967, incorporated herein by reference. Another suitable method involves the use of hydrated aluminum salts as given in U.S. Pat. No. 4,544,762, issued Oct. 1, 1985, incorporated herein by reference. Another suitable method is to use water which has been ultrasonically dispersed in a solvent as described in U.S. Pat. No. 4,730,071, issued Mar. 8, 1988, incorporated by reference herein or water which has been dispersed using high speed shearing as described in U.S. Pat. No. 4,730,072, issued Mar. 8, 1988 incorporated by reference herein.

A key aspect of this invention is the use of mixed methyl-ethyl aluminoxanes to produce the catalyst. The alkyl aluminoxane(s) used to produce the catalysts of the instant invention comprise one or more alkyl aluminoxanes wherein the alkyl is selected from the group consisting of methyl, ethyl and mixtures thereof and wherein the ratio of methyl groups to ethyl groups in the catalyst product falls within a defined range. The aluminoxane(s) utilized will have a ratio of methyl groups to ethyl groups ranging from about 4 to about 0.25, preferably from about 2 to about 0.33 and more preferably from about 1 to about 0.5. The mixed aluminoxanes are prepared from appropriate amounts of trimethyl aluminum, triethyl aluminum, diethylmethyl aluminum and ethyldimethyl aluminum as needed to provide the required ratio of methyl to ethyl. Trimethyl and triethyl aluminum compounds are more readily available than are the mixed methyl/ethyl aluminum compounds.

There are several substantially equivalent methods that can be used to prepare the mixed aluminoxane. For example, appropriate amounts of trimethyl aluminum and triethyl aluminum can be individually hydrolyzed and the resultant aluminoxanes combined to provide the desired mixture of methyl and ethyl aluminoxane. Also, trimethyl aluminum and triethyl aluminum can be mixed and the resultant mixture hydrolyzed to produce the desired mixture of methyl and ethyl aluminoxane. Methyldiethyl and dimethylethyl aluminum compounds, either alone or suitably mixed with each other or with trimethyl and/or triethyl aluminum can also be utilized.

In general terms the catalyst of the instant invention is prepared by reacting a zirconocene with the aluminoxane(s) in the presence of a suitable solvent. When only one alkyl aluminoxane is used, the alkyl will comprise a mixture of methyl and ethyl groups. When more than one alkyl aluminoxane is used, each alkyl aluminoxane may comprise individually either methyl aluminoxane or ethyl aluminoxane or a mixed methylethyl aluminoxane with the proviso that in the final product the methyl/ethyl ratio will fall within the defined range. The order of addition in contacting the zirconocene and aluminoxane(s) can vary. For example, the metallocene (neat or dissolved in a suitable solvent) can be first added to the reaction vessel followed by the addition thereto of the alumoxane(s); the alumoxane(s) and metallocene can be added to the reaction vessel simultaneously, the alumoxane(s) can be first added to the reaction vessel followed by the addition of the metallocene. Alternatively, a portion of the zirconocene can be reacted, for example, with methyl alumoxane, the remaining portion of the zirconocene reacted with ethyl alumoxane and then both reaction mixtures reacted together to produce the instant compositions. In accordance with the preferred embodiment of this invention the metallocene dissolved in a suitable inert hydrocarbon solvent is added to a stirred solution of the alumoxane(s).

The preparation of the metallocene-alumoxane reaction product, as mentioned above, is preferably conducted in an inert solvent, preferably a hydrocarbon solvent in which the metallocene and alumoxane or the reaction product of the metallocene and alumoxane are soluble. Preferred solutions include mineral oils and the various hydrocarbons which are liquid at reaction temperatures and in which the individual ingredients and/or the product are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deletereous effect of the reaction.

At all times, the individual ingredients as well as the recovered catalyst are protected from oxygen and moisture. Therefore, the reactions must be performed in an oxygen and moisture free atmosphere and recovered in an oxygen and moisture free atmosphere. Preferably, therefore, the reaction is performed in the presence of an inert dry gas such as, for example, helium or nitrogen. The recovered catalyst can be maintained in a nitrogen atmosphere, preferably at subambient temperature. The catalyst may also be stabilized by the addition of 3,3,3-trialkyl-1-propene as disclosed in U.S. Pat. No. 4,665,047, issued May 12, 1987.

The zirconocenes and aluminoxane are reacted to provide an atom ratio of Al to Zr of from about 1:1 to about 1:100, preferably from about 1:1 to about 1:50 more preferably from about 1:1 to about 1:20 and even more preferably from about 1:1 to about 1:10. Preferred are low ratios of from about 1:1 to about 1:5. Atom ratios of Al to Zr of less than 1:1 can be utilized. However, with these lesser limits a certain amount of the zirconocene will be "wasted" as a catalyst since the amount of zirconocene in excess of the equivalent amount of alumoxane will not be combined with the alumoxane and will not serve as a very effective catalyst. Although less effective, these lesser amounts are still considered within the scope of the instant invention. Atom ratios of Al to Zr of below 0.1 and more preferably below 0.5 are not particularly desired.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The present invention will now be illustrated by means of the following illustrative embodiments and examples which are provided for illustration and are not to be construed as limiting the invention.

The following abbreviations are used: Et for ethyl; Me for methyl; i-Bu for isobutyl; Cp for cyclopentadienyl; g.c. for gas chromatography. Molar amounts of an aluminoxane are determined on the basis of the molar amounts of trialkyl aluminum precurser used to prepare the aluminoxane. For example, one mole of aluminoxane and one mole of the trialkyl aluminum precursor used to prepare the aluminoxane are considered molar equivalents.

I. EXAMPLES

A. Preparation of Mixed Aluminoxane

32 Grams of $Al_2(SO_4) \cdot 18H_2O$ were ground to a powder and placed in a 500 ml. round bottomed flask fitted with a stopcock assembly for inlet and an outlet to a gas bubbler. 50 Milliliters of toluene which was dried with 3A molecular sieve was added to the flask, which was then purged with nitrogen while chilling in a wet ice bath. The toluene was stirred magnetically while adding 150 ml of 25% triethyl aluminum in n-heptane (calculated to be 0.28 mole of triethyl aluminum) and 50 ml of 25% trimethyl aluminum in toluene (calculated to be 0.14 mole trimethyl aluminum). The flask was maintained in the wet ice bath for the first four hours after addition, and then allowed to warm up to ambient temperature. 69 Hours after addition of the aluminum alkyl, the flask was stoppered under nitrogen and transferred to a dry box. The product was filtered and washed to solid with 25 ml of toluene. Solvent and aluminum alkyl were stripped on a rotary evaporator with gentle warming. 24 Grams were recovered.

B. Catalyst Preparation

The catalysts described in the following examples were prepared in situ as the catalyst ingredients and olefin substrate were warmed to reaction temperature while being mechanically stirred inside a dry box. The solvent, aluminoxane and bis(cyclopentadienyl)zirconium dichloride were placed in a dry, clean 100 ml Parr Autoclave. When a liquid olefin was to be used, it also was placed in the autoclave along with the catalyst components and the solvent. Gaseous olefin substrates, such as ethylene, propylene or 1-butene were introduced into the sealed autoclave under pressure. As the autoclave was heated to reaction temperature and the contents stirred, the catalyst components reacted to form the active catalyst in situ.

II. Oligomerization Procedure

The following illustrates the typical oligomerization procedures utilized in the oligomerization of ethylene.

Experiments were conducted with a 100 ml stirred Parr Autoclave. The catalyst and solvent were loaded in a dry box. The autoclave had previously been heated to remove moisture before introduction into the dry box. Solvents were dried over 3A molecular sieve and in the case of hydrocarbons, sodium was added for at least two days before use. After addition of materials to the autoclave, the vessel was weighed outside the dry box, and set up for stirring, heating and introduction of ethylene as quickly as possible. In some cases the autoclave was heated directly to near reaction temperature before addition of the ethylene. In other cases a small amount of ethylene was introduced to the autoclave during heatup. Heatup time was usually near three minutes before ethylene was added to bring the autoclave up to reaction pressure. Stirring was approximately at 700 RPM. Ethylene was c.p. grade and no attempt was made for further purification. After the reaction period, ethylene supply was shut off and the reactor was quickly cooled in a wet ice bath. The gas was vented and the reactor was reweighed to measure product weight. Nonane was added as an internal standard for gas chromatographic analysis on a capillary column.

A series of ethylene oligomerizations were carried out similar to that described above. The ethylene pressure was 200 psig. The reaction time was 0.5 hours. 2 Millimoles each of aluminoxane and $(Cp)_2 ZrCl_2$ were used to prepare the catalyst. 40 Milliliters of toluene was used in the autoclave as solvent. The reaction was carried out at the temperature specified in Table 1. The aluminoxane catalyst precursor was prepared by either hydrolyzing a mixture of $Et_3Al$ and $Me_3Al$ or by separately hydrolyzing $Et_3Al$ and $Me_3Al$ and combining separately. The catalyst was prepared in the autoclave by adding the $(Cp)_2ZrCl_2$ and the aluminoxane to the toluene solvent. The particular ethyl to methyl ratio used in the aluminoxane is shown in Table 1. The product was analyzed by g.c. and the results are shown in Table 1.

aluminoxane and differing solvents. 1-Butene was also added (in combination with ethylene) in one reaction. The aluminoxane had an ethyl to methyl ratio of 2. The

TABLE 1

| Example | Aluminoxane Ethyl:Methyl Ratio | RXN. Temp., °C. | Product Wt. G. | Product Distribution | | | | | | | | |
|---|---|---|---|---|---|---|---|---|---|---|---|---|
| | | | | $C_4$ | $C_6$ | $C_8$ | $C_{10}$ | $C_{12}$ | $C_{14}$ | $C_{16}$ | $C_{18}$ | $C_{20+}$ |
| 1-1 | 2:1[a] | 116-118 | 12.4 | 13.4 | 16.9 | 14.8 | 8.9 | 7.2 | 5.4 | 4.0 | 2.5 | 27.0 |
| 1-2 | 1:1[b] | 116-118 | 12.3 | 13.4 | 14.9 | 14.0 | 9.1 | 7.5 | 5.6 | 4.2 | 3.0 | 28.3 |
| 1-3 | 0:1[c] | 116-120 | 12.9 | 3.7 | 5.3 | 6.2 | 5.8 | 6.0 | 5.8 | 5.6 | 5.1 | 56.5 |
| 1-4 | 1:0[d] | 115-119 | 2.0 | 34.5 | 23.0 | 8.0 | 3.5 | 1.5 | 1.0 | 0.5 | 0 | 28.0 |
| 1-5 | 1:1[e] | 116-118 | 9.8 | 20.2 | 20.3 | 15.0 | 9.0 | 6.7 | 4.9 | 3.5 | 2.1 | 18.3 |
| 1-6 | 2:1[a] | 105-110 | 24.8 | 13.2 | 4.6 | 6.5 | 5.8 | 6.3 | 5.0 | 4.2 | 3.1 | 51.3 |

[a] Aluminoxane prepared by controlled hydrolysis of a 2:1 mixture of $Et_3Al$ and $Me_3Al$ with $Al_2(SO_4)_3 \cdot 18H_2O$.
[b] Aluminoxane prepared by controlled hydrolysis of a 1:1 mixture of $Et_3Al$ and $Me_3Al$ with $Al_2(SO_4)_3 \cdot 18H_2O$.
[c] Aluminoxane prepared by controlled hydrolysis of $Me_3Al$ with $Al_2(SO_4)_3 \cdot 18H_2O$.
[d] Aluminoxane prepared by controlled hydrolysis of $Et_3Al$ with $Al_2(SO_4)_3 \cdot 18H_2O$.
[e] Methylaluminoxane and ethylaluminoxane were prepared separately and then mixed in the reactor.

The above experiments were repeated but using 3 mmoles of aluminoxane and 2 mmoles of $(Cp)_2ZrCl_2$. The reaction temperature was 115°-119° C., pressure was 200 psig and time was 0.5 hours. Aluminoxanes prepared individually from $Me_3Al$, $Et_3Al$ and $(i-Bu)_3Al$ were also used for comparison purposes. The results are shown in Table 2.

TABLE 2

| Example | Aluminoxane Et:Me:i-Bu | Product Wt. G. | Product Distribution | | | | | | | | |
|---|---|---|---|---|---|---|---|---|---|---|---|
| | | | $C_4$ | $C_6$ | $C_8$ | $C_{10}$ | $C_{12}$ | $C_{14}$ | $C_{16}$ | $C_{18}$ | $C_{20+}$ |
| 2-1 | 2:1:0[a] | 12.4 | 26 | 22.3 | 15.4 | 10.1 | 5.7 | 3.5 | 2.7 | 1.0 | 13.3 |
| 2-2 | 1:1:0[b] | 19.4 | 13.7 | 14.7 | 12.6 | 9.7 | 8.4 | 7.3 | 6.1 | 5.0 | 22.5 |
| 2-3 | 0:1:0[c] | 9.2 | 3.3 | 4.1 | 5.1 | 5.0 | 5.3 | 5.6 | 5.3 | 5.0 | 61.3 |
| 2-4 | 1:0:0[d] | 2.7 | 32.6 | 27.8 | 11.8 | 5.2 | 2.6 | 1.1 | 0.7 | 0.3 | 17.9 |
| 2-5 | 1:1:0[e] | 19.3 | 13.8 | 16.3 | 14.5 | 10.0 | 8.1 | 6.4 | 5.0 | 3.8 | 22.1 |
| 2-6 | 0:1:1[f] | 10.6 | 3.9 | 4.2 | 6.5 | 6.5 | 5.2 | 5.0 | 4.7 | 4.4 | 59.6 |
| 2-7 | 0:0:1[g] | 2.0 | — | — | — | — | — | — | — | — | — |

[a] Aluminoxane prepared by controlled hydrolysis of a 2:1 mixture of $Et_3Al$ and $Me_3Al$ with $Al_2(SO_4)_3 \cdot 18H_2O$.
[b] Aluminoxane prepared by controlled hydrolysis of a 1:1 mixture of $Et_3Al$ and $Me_3Al$ with $Al_2(SO_4)_3 \cdot 18H_2O$.
[c] Aluminoxane prepared by controlled hydrolysis of $Me_3Al$ with $Al_2(SO_4)_3 \cdot 18H_2O$.
[d] Aluminoxane prepared by controlled hydrolysis of $Et_3Al$ with $Al_2(SO_4)_3 \cdot 18H_2O$.
[e] Methylaluminoxane and ethylaluminoxane were prepared separately and then mixed in the reactor.
[f] Methylaluminoxane and isobutylaluminoxane were prepared separately and then mixed in the reactor.
[g] Aluminoxane prepared by controlled hydrolysis of tri-isobutylaluminum with $Al_2(SO_4)_3 \cdot 18H_2O$.

Additional experiments were carried out as above using differing pressures, amounts of zirconocene, aluminoxane and differing solvents. 1-Butene was also added (in combination with ethylene) in one reaction. The aluminoxane had an ethyl to methyl ratio of 2. The reaction time was 0.5 hours. The results are shown in Table 3.

TABLE 3

| Example | $Cp_2ZrCl_2$ mmoles | Aluminoxane Compound mmoles[c] | Solvent, ml | 1-Butene gms | Ethylene psig |
|---|---|---|---|---|---|
| 3-1 | 3 | 2 | N-heptane 40 ml | 0 | 200 |
| 3-2 | 3 | 2 | Toluene 40 ml | 0 | 200 |
| 3-3 | 1 | 2 | Toluene 40 ml | 0 | 160 |
| 3-4 | 1 | 8 | Toluene 40 ml | 0 | 160 |
| 3-5 | 2 | 2 | Heptane 20 ml | 7.5 | 200 |

| Example | RXN Temp °C. | Product Wt. $C_4$-$C_{18}$ gms | | Product $C_{20+}$ % | Straight-Chain Alpha Olefins % | Vinylidene Olefins % | Internal Olefins % |
|---|---|---|---|---|---|---|---|
| | | gms | % | | | | |
| 3-1 | 110-116 | 11.9 | 58 | 42 | 87[a] | 4[a] | 9[a] |
| 3-2 | 117-120 | 13.2 | 80.3 | 19.7 | 91[b] | ? | ? |
| 3-3 | 116-120 | 9.2 | 73.4 | 26.6 | 87.5[b] | ? | ? |
| 3-4 | 115-119 | 13.7 | 69 | 31 | 58.4[b] | ? | ? |
| 3-5 | 115-118 | 8.9 | 81.5 | 18.5 | 70[a] | 21[a] | 8[a] |

[a] Determined by $C^{13}$NMR.
[b] GC analyses of the $C_{10}$ component allowed for alpha olefin determination but not a distinction between vinylidene olefins and straight chain internal olefins which constituted the remainder.
[c] Basis atomic aluminum, that is, one mole of aluminoxane is considered equivalent to one mole of trialkyl aluminum precursor.

We claim:
1. An olefin oligomerization catalyst comprising the reaction product of a zirconocene and one or more alkyl aluminoxanes wherein alkyl is a mixture of methyl and ethyl groups, wherein the ratio of equivalents of methyl to ethyl ranges from about 4 to about 0.25, and wherein the atom ratio of aluminum to zirconium ranges from about 0.1 to about 100.

2. The catalyst of claim 1 wherein the ratio of methyl to ethyl ranges from about 2 to about 0.33.

3. The catalyst of claim 2 wherein the ratio of methyl to ethyl ranges from about 1 to about 0.5.

4. The catalyst of any one of claims 1–3 wherein the zirconocene has the general formula (cyclopentadienyl)$_n$ZrY$_{4-n}$ wherein n is an integer ranging from 1 to 4, Y is selected from the group consisting of hydrogen, a $C_1$–$C_5$ alkyl group, a $C_6$–$C_{20}$ aryl group and halogen.

5. The catalyst of claim 4 wherein the zirconocene is selected from bis(cyclopentadienyl)zirconium dichloride, bis(cyclopentadienyl)zirconium methyl chloride, bis(cyclopentadienyl)zirconium dimethyl, bis(methylcyclopentadienyl)zirconium dichloride, bis(methylcyclopentadienyl)zirconium methyl chloride, bis(methylcyclopentadienyl)zirconium dimethyl, bis(pentamethylcyclopentadienyl)zirconium dichloride, bis(pentamethylcyclopentadienyl)zirconium methyl chloride, bis(pentamethylcyclopentadienyl)zirconium dimethyl, bis(n-butyl-cyclopentadienyl)zirconium dichloride, bis(n-butylcyclopentadienyl)zirconium methyl chloride, bis(n-butyl-cyclopentadienyl)zirconium dimethyl.

6. The catalyst of claim 4 wherein the atom ratio of aluminum to zirconium ranges from about 1 to about 20.

7. The catalyst of claim 6 wherein the atom ratio of aluminum to zirconium ranges from about 1 to about 10.

8. The catalyst of claim 7 wherein the atom ratio of aluminum to zirconium ranges from about 1 to about 5.

9. The catalyst of any one of claims 1–3 wherein the alkyl aluminoxane is prepared by hydrolyzing a mixture of trimethyl aluminum and triethyl aluminum compounds.

10. The catalyst of any one of claims 1–3 wherein the alkyl aluminoxane is prepared by separately hydrolyzing trimethyl aluminum and triethyl aluminum and mixing the resultant aluminoxanes together.

11. A process for oligomerizing olefins comprising ethylene which comprises contacting said olefins at a temperature ranging from about 100° to about 130° C. with a catalyst comprising the reaction product of a zirconocene and one or more alkyl aluminoxanes wherein alkyl is a mixture of methyl and ethyl groups, wherein the ratio of equivalents of methyl to ethyl ranges from about 4 to about 0.25, and wherein the atom ratio of aluminum to zirconium ranges from about 0.1 to about 100.

12. The process of claim 11 wherein the catalyst the ratio of methyl to ethyl ranges from about 2 to about 0.33.

13. The process of claim 12 wherein in the catalyst the ratio of methyl to ethyl ranges from about 1 to about 0.5.

14. The process of claim 11 wherein the temperature ranges from about 110° to about 125° C.

15. The process of claim 11 wherein the temperature ranges from about 115° to about 120° C.

16. The process of claim 12 wherein the temperature ranges from about 110° to about 125° C.

17. The process of claim 12 wherein the temperature ranges from about 115° to about 120° C.

18. The process of claim 13 wherein the temperature ranges from about 110° to about 125° C.

19. The process of claim 13 wherein the temperature ranges from about 115° to about 120° C.

20. The process of any one of claims 11–19 wherein the olefins being oligomerized additionally comprise one or more $C_3$ to $C_{10}$ alpha olefins.

21. The process of any one of claims 11–19 wherein in the catalyst the zirconocene has the general formula (cyclopentadienyl)n-ZrY$_{4-n}$ wherein n is an integer ranging from 1 to 4, Y is selected from the group consisting of hydrogen, a $C_1$–$C_5$ alkyl group, a $C_6$–$C_{20}$ aryl group and halogen.

22. The process of claim 21 wherein in the catalyst the zirconocene is selected from bis(cyclopentadienyl)zirconium dichloride, bis(cyclopentadienyl)zirconium methyl chloride, bis(cyclopentadienylzirconium dimethyl, bis(methylcyclopentadienyl)zirconium dichloride, bis(methylcyclopentadienyl)zirconium methyl chloride, bis(methylcyclopentadienyl)zirconium dimethyl, bis(pentamethylcyclopentadienyl)zirconium dichloride, bis(pentamethylcyclopentadienyl)zirconium methyl chloride, bis(pentamethylcyclopentadienyl)zirconium dimethyl, bis(n-butyl-cyclopentadienyl)zirconium dichloride, bis(n-butylcyclopentadienyl)zirconium methyl chloride, bis(n-butylcyclopentadienyl)zirconium dimethyl.

23. The process of claim 21 wherein in the catalyst the atom ratio of aluminum to zirconium ranges from about 1 to about 20.

24. The process of claim 23 wherein in the catalyst the atom ratio of aluminum to zirconium ranges from about 1 to about 10.

25. The process of claim 24 wherein in the catalyst the atom ratio of aluminum to zirconium ranges from about 1 to about 5.

26. The process of any one of claims 11–19 wherein in the catalyst the alkyl aluminoxane is prepared by hydrolyzing a mixture of trimethyl aluminum and triethyl aluminum compounds.

27. The process of any one of claims 11–19 wherein in the catalyst the alkyl aluminoxane is prepared by separately hydrolyzing trimethyl aluminum and triethyl aluminum and mixing the resultant aluminoxanes together.

28. The process of any one of claims 11–19 wherein the olefins being oligomerized additionally comprise one or more $C_3$ to $C_{10}$ alpha olefins.

* * * * *